(12) United States Patent  
Thompson et al.

(10) Patent No.: US 8,789,951 B2  
(45) Date of Patent: Jul. 29, 2014

(54) INTRA-OCULAR LENS OPTIMIZER

(71) Applicant: DigitalVision, LLC, Atlanta, GA (US)

(72) Inventors: Keith P. Thompson, Atlanta, GA (US); Jose R. Garcia, Mableton, GA (US)

(73) Assignee: DigitalVision, LLC, Atlanta, GA (US)

( * ) Notice: Subject to any disclaimer, the term of this patent is extended or adjusted under 35 U.S.C. 154(b) by 0 days.

(21) Appl. No.: 13/738,777

(22) Filed: Jan. 10, 2013

(65) Prior Publication Data

US 2013/0176536 A1 Jul. 11, 2013

Related U.S. Application Data

(60) Provisional application No. 61/585,104, filed on Jan. 10, 2012.

(51) Int. Cl.
*A61B 3/02* (2006.01)

(52) U.S. Cl.
USPC ........................... 351/233; 351/237; 351/239

(58) Field of Classification Search
USPC ................................................. 351/200–246
See application file for complete search history.

(56) References Cited

U.S. PATENT DOCUMENTS

| | | |
|---|---|---|
| 3,305,294 A | 2/1967 | Alvarez |
| 3,860,330 A | 1/1975 | Persson |
| 3,874,774 A | 4/1975 | Humphrey |
| 4,015,899 A | 4/1977 | Humphrey |
| 4,043,644 A | 8/1977 | Humphrey |
| 4,385,813 A | 5/1983 | Klein et al. |
| 4,523,822 A | 6/1985 | Thurston |
| 4,820,040 A | 4/1989 | Sims |
| 5,258,791 A | 11/1993 | Penney et al. |
| 5,532,770 A | 7/1996 | Scheider et al. |
| 5,875,017 A | 2/1999 | Ohuma et al. |
| 6,685,741 B2 | 2/2004 | Landreville et al. |
| 6,688,745 B2 | 2/2004 | Ross et al. |
| 6,709,108 B2 | 3/2004 | Levine et al. |
| 6,722,767 B2 | 4/2004 | Dick et al. |
| 6,827,442 B2 | 12/2004 | Ross et al. |
| 6,932,475 B2 | 8/2005 | Molebny et al. |

(Continued)

OTHER PUBLICATIONS

International Search Report for PCT/US2013/021059, Jan. 10, 2013.

*Primary Examiner* — Mohammed Hasan
(74) *Attorney, Agent, or Firm* — McClure, Qualey & Rodack, LLP (57) ABSTRACT

A vision testing method and apparatus are disclosed, the method including measuring the modulation to a wavefront of light that is imparted by an intra-ocular lens, determining the wavefront modulation necessary to emulate the optical properties of the IOL after it replaces the crystalline lens in a patient's eye, generating a static or dynamic image viewable by a patient, modulating the wavefront of the image remote from the patient to attain the wavefront that necessary to emulate the optical properties of the IOL after it is implanted, and relaying said wavefront to a plane nearby, on, or within the patient's eye. The apparatus includes devices for measuring the modulation to a wavefront of light that is imparted by an intra-ocular lens, determining the wavefront modulation necessary to emulate the optical properties of the IOL after implantation in a patient's eye, generating a static or dynamic image viewable by a patient, modulating the wavefront of the image remote from the patient to attain the wavefront necessary to emulate the optical properties of the IOL after it is implanted, and relaying said wavefront to a plane nearby, on, or within the patient's eye.

11 Claims, 11 Drawing Sheets

(56) References Cited

U.S. PATENT DOCUMENTS

| | | |
|---|---|---|
| 6,964,480 B2 | 11/2005 | Levine |
| 6,997,555 B2 | 2/2006 | Dick et al. |
| 7,195,354 B2 | 3/2007 | Olivier et al. |
| 7,303,281 B2 * | 12/2007 | Wakil et al. ............. 351/246 |
| 7,387,387 B2 | 6/2008 | Dai |
| 7,425,068 B2 | 9/2008 | Koest |
| 7,553,022 B2 | 6/2009 | Neal et al. |
| 7,654,672 B2 | 2/2010 | Zhao et al. |
| 7,703,919 B2 | 4/2010 | Thompson et al. |
| 7,708,410 B2 | 5/2010 | Dai |
| 7,717,558 B2 | 5/2010 | Hong et al. |
| 7,815,310 B2 | 10/2010 | Su et al. |
| 7,909,463 B2 | 3/2011 | Dick et al. |
| 7,926,944 B2 | 4/2011 | Thompson et al. |
| 8,118,427 B2 | 2/2012 | Bonnin et al. |
| 2011/0001930 A1 | 1/2011 | Levecq |
| 2011/0080562 A1 | 4/2011 | Iizuka et al. |
| 2011/0228226 A1 | 9/2011 | Pixton et al. |
| 2013/0182215 A1 * | 7/2013 | Tung ................. 351/159.05 |

* cited by examiner

| No. | Lens Element |
|---|---|
| 29 | Accessory |
| 30 | Accessory |
| 31 | Spherical Aberration Element A |
| 32 | Spherical Aberration Element B |
| 33 | Comatic Element A |
| 34 | Comatic Element B |
| 35 | 0°-90° Jackson Cross Cylinder Element A |
| 36 | 0°-90° Jackson Cross Cylinder Element B |
| 37 | 45°-135° Jackson Cross Cylinder Element A |
| 38 | 45°-135° Jackson Cross Cylinder Element B |
| 39 | Spherical Element A |
| 40 | Spherical Element B |
| 41 | Accessory |
| 42 | Accessory |
| 43 | Accessory |
| 44 | Accessory |
| 45 | Accessory |

INTRA-OCULAR LENS OPTIMIZER

BACKGROUND OF THE DISCLOSURE

1. Field

Disclosed is a method and apparatus of simulating the optical properties of one or more intraocular lenses following implantation under real-world conditions at far away, close, and intermediate distances, and under monocular or binocular viewing conditions.

2. Description of the Related Art

Some fundamental optical concepts concerning presbyopia, cataracts, and cataract extraction and implantation of intraocular lenses are provided in order to facilitate an understanding of the method and apparatus.

The convergence, or divergence, of light rays from an object is measured in optical units known as Diopters "D" where D=1/F, and F is the distance between the object and its image in Meters. By convention, converging light is designated by a positive sign (+D) and diverging light is designated by a negative sign (−D).

A normal eye has a converging optical power at rest of about +60D and it focuses distance objects to a clear focus on the retina. About two-thirds of the eye's optical power is provided by the corneal surface and the remainder of the optical power is provided by the crystalline lens inside the eye.

The image of an object 6M away has a diverging power of ⅙ D, a value which is insignificant relative to the total optical power of the eye. Clinicians skilled in the art consider objects at 6M, or beyond, to have optical properties that are similar to objects located at infinite distances.

An object located 1 meter from the eye produces light rays that have a divergence of −1 D and an object at 0.25M, a typical reading distance, produces light rays with −4D of divergence. The divergence of light rays from these nearby objects must be neutralized by the eye in order to focus the image of the near object sharply on the retina where it can be perceived clearly.

In youth, the additional optical power needed is provided by the crystalline lens inside the eye which becomes more spherical and more optically powerful when attention is focused on near objects. The triad of actions that occur when viewing a near object consists of convergence, or nasal deviation, of the optical axes of the eyes; miosis—a decrease in the diameter of the pupils; and accommodation—an increase in the optical power of the crystalline lens thereby providing the additional focusing power needed for viewing near objects clearly.

Presbyopia is the age-related loss of accommodation, which requires middle-aged patients to wear reading glasses or bifocals to see near objects clearly. Patients who have had their crystalline lens removed due to cataract, trauma, or other disease are, in effect, presbyopic, and they must wear optical correction for clear near vision.

A cataract is a clouding of the eye's clear crystalline lens that impairs vision. Cataracts are most commonly caused by aging processes in the lens. Once the leading cause of blindness, cataracts are now treated effectively by removal of the opaque natural lens, or cataract, and by the implantation of an intraocular lens, or "IOL," to restore vision. In the United States, cataract surgery is the most commonly performed surgical procedure with about 3.5 M procedures performed in 2010.

Initially, patients who had cataracts removed had to wear very powerful, thick spectacle lenses to restore the optical power of the crystalline lens that was removed. These "aphakic spectacles" caused distortion of objects and caused the patient's eyes to appear abnormally large to others. However, without their thick aphakic spectacles, these patients were functionally blind.

Subsequent development of contact lenses with high plus power to restore the power of the crystalline lens that was removed (aphakic contact lenses) provided patients with improved optical performance and cosmetic appearance following cataract extraction.

In WWII, Harold Ridley, a British surgeon, observed that plastic shards that penetrated the eyes of aviators were well tolerated for long periods of time. Based upon his observations, Ridley devised a plastic intraocular lens replacement to restore the optical function of the crystalline lens that was removed during cataract surgery. Ridley's work spawned the evolution of modern intraocular lens implants (IOLs) which have undergone significant improvements in optical designs and materials during the last 50 years.

Today, modern cataract surgery with the implantation of an intraocular lens using soft acrylic, silicone, hydrogel, and other biocompatible polymeric materials is commonly performed and considered to be the standard of medical practice in the United States and developed countries around the world.

The first intraocular lenses had a single optical power that was generally selected to provide the patient with good distance vision following surgery. For intermediate and near distances, reading glasses such as bifocals, trifocals, or multifocal progressive add spectacle lenses (PALs) were prescribed following surgery.

Advancements in lens manufacturing techniques and in the understanding of physiological optics permitted the development of more complex IOL designs for the correction of astigmatism. More recently, presbyopia-correcting IOLs have been developed. The purpose of presbyopia correcting IOLs is to provide the post cataract surgery patient with satisfactory distance, intermediate, and near vision that permits them to conduct their daily activities without glasses.

Presbyopia Correcting IOLs (PC-IOLs).

Presbyopia correcting IOLs of refractive, diffractive, and accommodative designs are known.

The refractive type of presbyopia correcting intraocular lens has a lens surface that is composed of different surface areas, each with different radii of curvature with transitional regions that have aspherical curvatures. The diffractive type of presbyopia correcting IOL employs a diffractive, or Fresnel lens array, an optical design that features alternating rings of lenslets, each possessing a different optical power. Presbyopia correcting IOLs of accommodating designs are designed to move along the optical axis of the eye in response to changes in the ciliary muscle that occur when the patient views a near object, thereby increasing the effective optical power of the IOL.

Each type of presbyopia correcting IOL has advantages and disadvantages. Diffractive IOLs have predictable near add power, but they scatter approximately 20% of the light and degrade image quality to a degree that some patients find unacceptable. Presbyopia-correcting IOLs of refractive designs may be particularly sensitive to the size of the pupil and to decentration and tilt of the IOL. Accommodative lenses may not always couple to the delicate intraocular structures and move in the way their designers intended.

Within each type of presbyopia correcting IOL, there are numerous lenses with variations in design that reflect the philosophy and experience of the lens manufacturer. Examples of presbyopia correcting IOLs may be found in U.S. Pat. Nos. 7,717,558 and 6,685,741.

Despite the potential for presbyopia correcting IOLs to free post-cataract surgery patients from the need to wear corrective eyewear after surgery, there are major unsolved problems with prior art methods for selecting appropriate candidates for PC-IOL surgery, for identifying patients who will be dissatisfied with their implant, for determining which lens design will work best for a given patient, and for improving the designs of PC-IOLs.

In most instances, the patient must pay an out of pocket fee for a presbyopia correcting IOL in addition to what is covered by Medicare and private insurance programs. There are presently limited and ineffective tools available to demonstrate to the patient the benefit that a presbyopia correcting IOL will provide in comparison to the vision that a monofocal IOL provides. Thus, patients are presently asked to pay a considerable fee for a benefit that cannot be realistically demonstrated to them before surgery.

As more and more presbyopia correcting IOLs become available, ophthalmologists and their patients are exposed to an expanding number of choices and marketing claims that are difficult to evaluate objectively. Unlike the shopper who may try on a new shoe to assess its fit and comfort before purchase, patients cannot presently preview and compare the vision that will be provided by different IOL designs prior to their cataract-IOL surgery.

Clinical experience with PC-IOLs has demonstrated that not all patients are good candidates for these lenses. Some patients are so dissatisfied with their vision following surgery that the PC-IOL must be explanted and replaced by a lens of different design. A lens exchange procedure subjects the patient to the additional risks and costs of surgery.

It has been reported that patients who are highly detail-oriented and/or who have demanding personalities are poor candidates for PC-IOL surgery, yet there are no commonly accepted objective standards for making such an assessment. Some surgeons believe that patients who have undergone prior corneal refractive surgery such as radial keratotomy (RK) or laser vision surgery (PRK or LASIK) should not receive any type of presbyopia correcting IOL. Yet, other surgeons favor the implantation of a particular presbyopia correcting IOL for these patients. Some surgeons recommend that presbyopia correcting lenses of different design be implanted in each eye, a so-called mix and match approach. Yet, other surgeons dissuade such a strategy.

Confounding the lack of consensus on standards for selecting presbyopia correcting IOLs is the fact that patients have different lifestyles and different visual needs and the different IOL designs vary in their ability to meet these visual needs following surgery.

Measurement of Intra-Ocular Lenses.

Methods to measure the optical properties of IOLs are known. U.S. Pat. No. 7,944,533 to Alcon, Inc. teaches a method of measuring a multifocal diffractive IOL by using a Hartmann Schack wavefront sensor that has a sufficiently dense array of lenslets to measure the optical properties of the IOL.

Spatially resolved refractometers are known, such as the device described by Webb in U.S. Pat. No. 6,000,800. A spatially resolved refractometer may be modified to determine the optical characteristics of a 6 mm diameter IOL by introducing an aperture that is small relative to the optical component measured. For example, a diffractive IOL may have rings of 0.25 mm in width. Therefore an appropriate aperture size of 0.1 mm may be selected to scan and characterize the optical properties of the IOL.

Wave Plates.

Wave plates that impart a phase change to the wavefront of an image are known. A suitable wave plate may be manufactured from PMMA or other optically suitable material using laser fabrication means or by computer controlled lathe means.

Means to emulate the outcome of a surgical procedure are known by those skilled in the art. For example, monovision can be emulated by trial of contact lenses that approximate the outcome that can be expected following laser vision surgery. Wave plates to simulate outcomes of laser vision procedures are known as well.

IOL Simulators.

Multifocal IOL simulators are known such as the device described in US Patent application US 2011/0080562. This application teaches a multifocal intraocular lens simulator that includes an optical system that allows an object to be observed through it, and a test lens holder which holds a prescribed test intraocular lens. The intraocular lens holder is installed at a position optically conjugate with a position at which an eye of an observer is to be placed.

The prior art method of simulating a multifocal lens does not provide the patient a realistic assessment of the quality of vision that the multi-focal IOL will provide, because no means are provided to view objects of varying size, shape, color, contrast, and illumination; nor does the aforementioned patent application teach a means to view objects at near, intermediate, and far away distances.

Prior art devices provide no clinically practical method for determining which, if any, of the available designs of presbyopia correcting IOLs will provide a given patient with a satisfactory level of visual function following implantation of an intraocular lens, nor do they permit the patient to preview, compare, and select the IOL design that they prefer based upon a comparison of the IOLs image producing properties.

Unsolved Problems.

As a result of these unsolved problems, the market adoption of PC-IOLs has been far below predicted values as many patients and surgeons have low confidence in the patient's satisfaction with the vision provided by the PC-IOL. The inability to assess the performance of different lens designs without implantation has slowed the innovation improved designs.

To address these unsolved problems, this disclosure teaches a new method and apparatus that permits patients to preview and compare the distant, intermediate, and near vision that a particular IOL lens design will provide, and allow the patient to compare the vision provided by a plurality of designs while observing realistic images of real-world scenes over a variety of viewing distances. This provides patients, before surgery, the ability to preview, compare, and select the IOL lens design that is most likely to provide satisfactory visual function following surgery.

SUMMARY

An intra-ocular lens optimizer is disclosed. An optical device is provided that measures the modulations to the wavefront of an image that passes through an intraocular lens "IOL." An IOL vision emulator is provided comprised of an exam chair, a wavefront generator with a plurality of independent channels, and a focusing system.

In the wavefront generator, a projector, preferentially a digital display, projects a real image through optical elements that are under control of a computer. A focusing system, preferentially a spherical field mirror, focuses the wavefront generator to a position that is optically conjugate to the patient's eye. The focusing system may provide a near-viewing display accessory that can be placed at variable distances from the patient for near and intermediate viewing conditions and an eye tracker to stabilize the positions of the projected images.

The refractive error of the visual system of the eye being tested is nulled by the wavefront generator and the wavefront generator is then adjusted to produce an image on the patient's retina that emulates the image that would result if the IOL was implanted in the patient's eye following cataract extraction.

The disclosure teaches the ability to test the tolerance of prospective implant patients to different IOL designs over a range of different distances and viewing conditions under monocular or binocular conditions. This permits IOL emulation under natural conditions, void of obstructing instruments, and it allows the patient to preview, compare, and select the IOL design, from a plurality of designs, that provides optimal eyesight with minimal visual side effects.

DETAILED DESCRIPTION

One embodiment of the apparatus has two components. An IOL measurement means is used to characterize the optical properties of one or more IOLs and to determine the modulation of the wavefront of an image that is necessary to reproduce or emulate the optical properties of the IOL once it is implanted in the patient's eye following removal of the patient's crystalline lens. The second component is an IOL emulator means that recreates the optical properties of the IOL for patient testing. In an alternative embodiment, the optical properties of the IOL are provided elsewhere.

Figure 1:
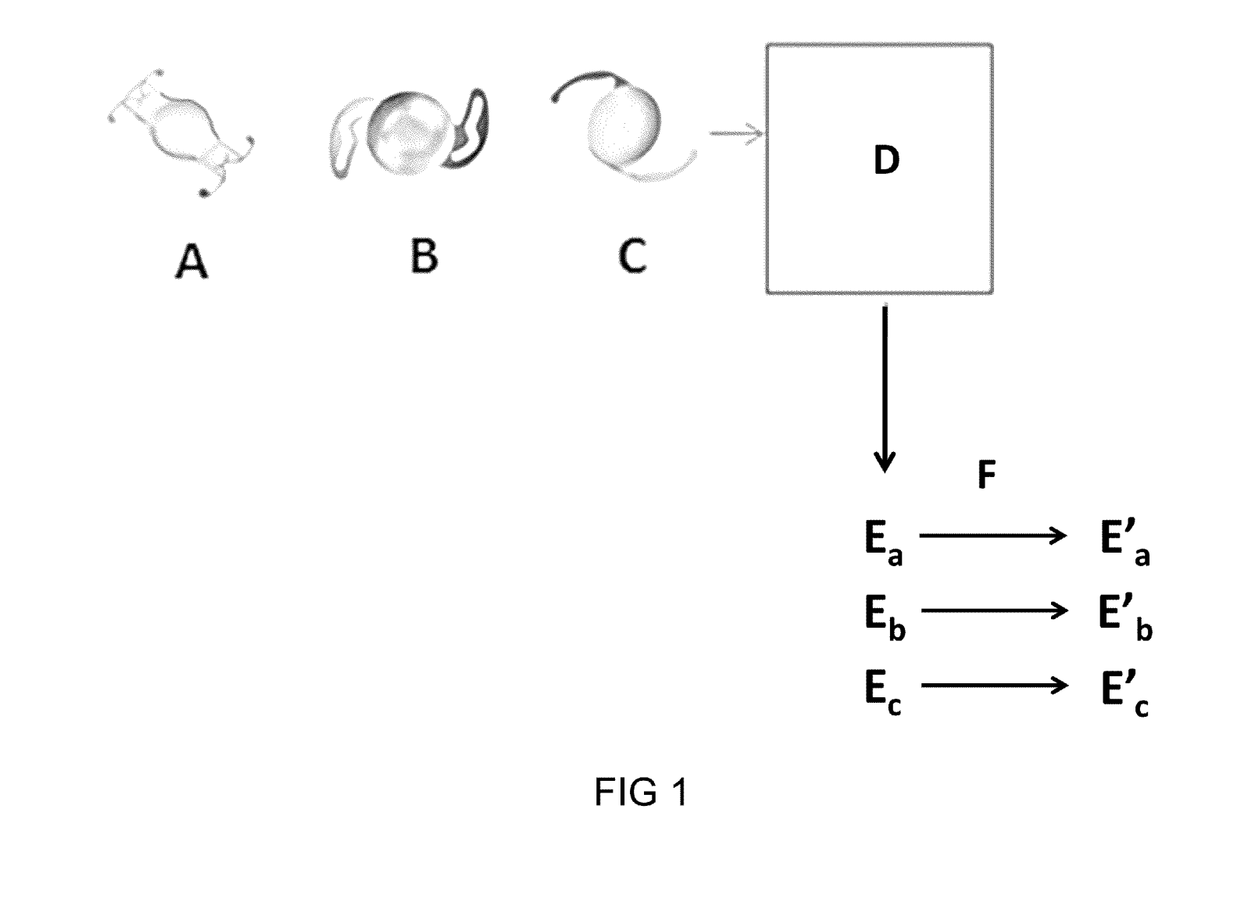
FIG. 1 is a diagram showing diagrams of intraocular lenses (IOLs) of three different types and an IOL measuring means that is used to measure the optical properties of the IOLs.

FIG. 1 shows three multi-focal IOLs A, B, C that are made by different manufacturers and that have different optical designs. Three lenses are shown for exemplary purposes to illustrate the three major types of presbyopia correcting IOLs in use today; refractive, diffractive, and accommodating. The instrument is not limited to emulating these types of designs and it may be used to measure and emulate new IOL designs that are developed in the future. In addition, the instrument can be used to measure any number of designs of a given type but that vary in their design characteristics, dimensions, materials, and/or other properties. Optical characterization means D, is used to characterize the optical properties of each IOL, independently. Such optical characterization means suitable for use in this apparatus are known. In a preferred embodiment, optical characterization means D may be a spatially resolved refractometer, a Schack-Hartmann wavefront sensor, or an atomic surface profiler. In addition to measuring the phase change imparted to an image by the IOL, the change in image intensity and/or image intensity as a function of wavelength can be measured by a suitable device such as a spectrometer. Following measurement with optical characterization means D, the optical properties of the IOL may be described by a mathematical function E, for example by a Zernicke series or a Fournier transform series function. Those skilled in the art are familiar with these, and other mathematical functions, that may be used to describe the phase changes, or modulation to the wavefront of light, that occurs as light passes through the IOL.

It is also known to those skilled in the art that the total phase change imparted to a wave of light by an IOL is a function of both the shape of the front and back surfaces of the IOL and the difference between the index of refraction of the IOL and the index of refraction of the medium surrounding the IOL. The index of refraction of a material is a ratio of the speed of light in a vacuum to the speed of light through the material. Because the IOL is designed to be implanted in the eye, and it is known that fluids in the eye that surround the IOL have a refractive index of approximately 1.3, appropriate correction factors can be applied to accurately determine the optical properties of the IOL when it is implanted in the eye even though the measurements of the IOL were made in air.

Figure 2:
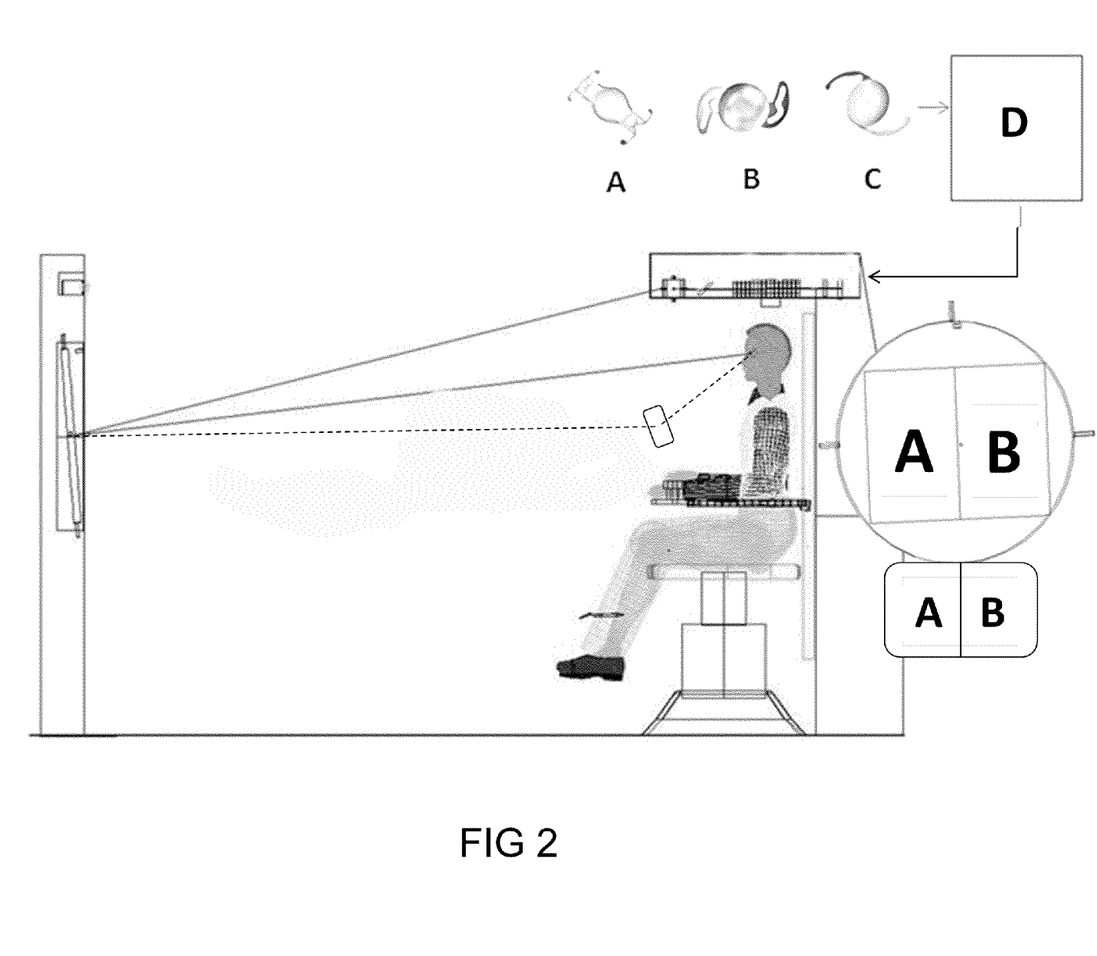
FIG. 2 is a diagrammatical side elevational view of the apparatus depicting the patient's view of images produced by different IOLs to be emulated.
Figure 3:
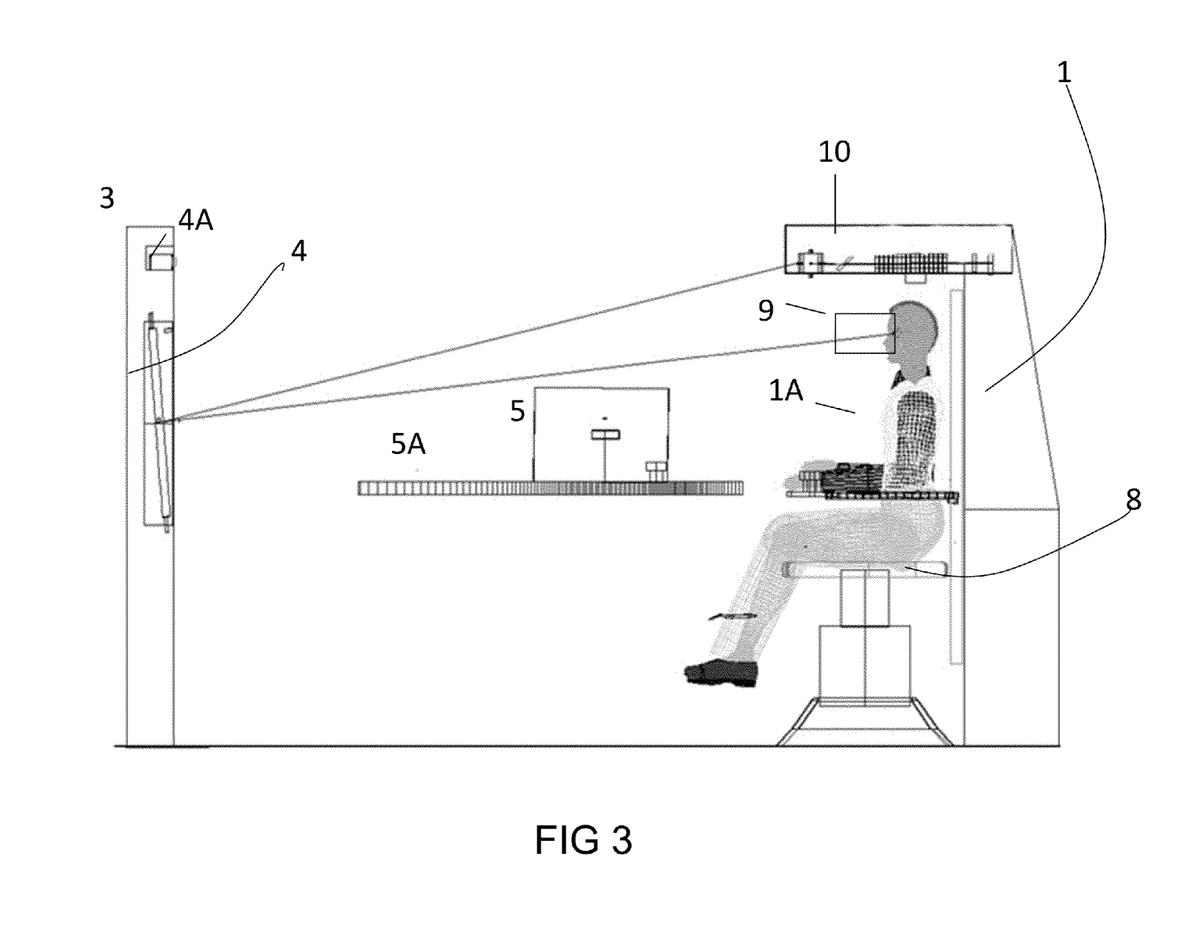
FIG. 3 is a diagrammatical side elevational view of the patient chair and rear tower of the IOL emulator.
Figure 4:
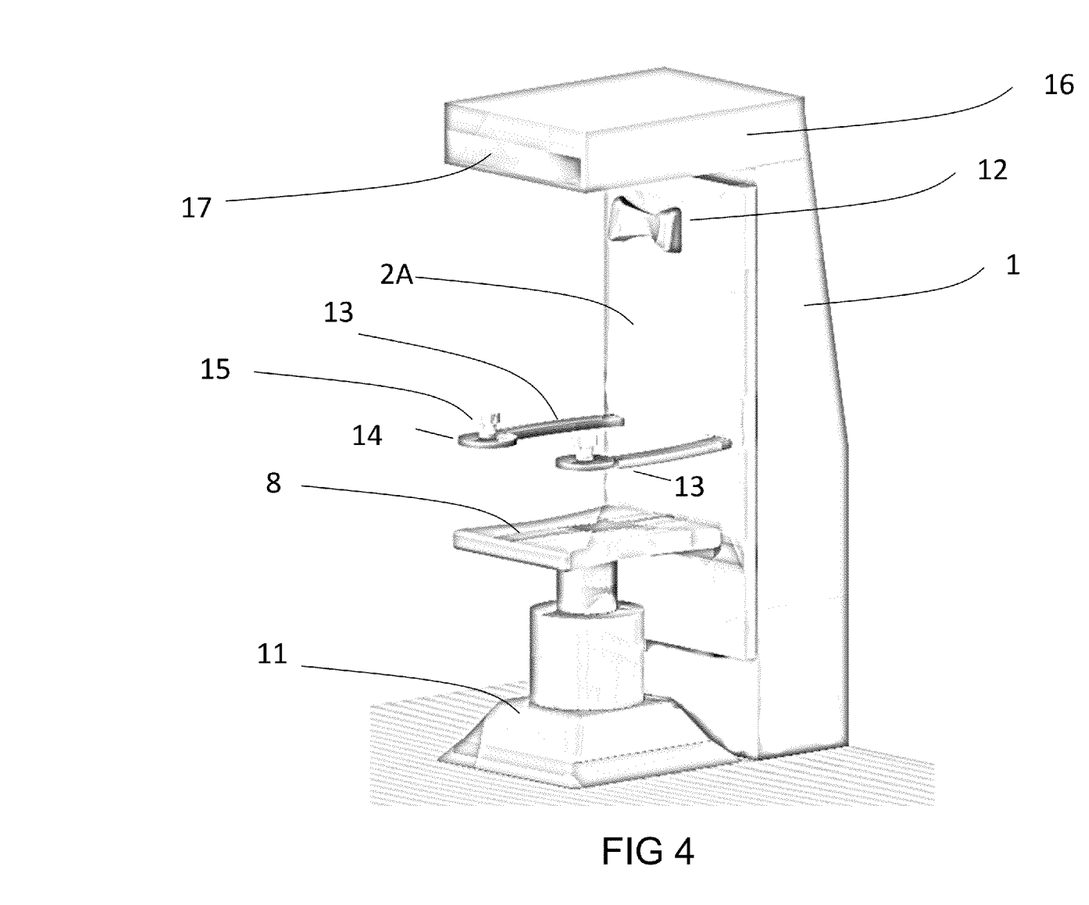
FIG. 4 is a perspective view of the apparatus.

FIGS. 2-4 show the IOL emulation apparatus. The IOL emulation apparatus consists of tower 1, an examination chair 2A, a viewport 3 which houses a reflective field mirror 4 and optional camera 4A, and an operator control terminal 5. The patient 1A undergoing vision testing with IOL emulator is seated in the examination chair seat 8 which is adjusted to place the patient's eyes within the desired examination position noted by box 9. Images are generated by optical elements in the wavefront generator 10 and directed to a field mirror 4 in the viewport 3 where they are reflected to the patient's eyes located within the desired examination position 9. Behind the patient, rear cabinet 1 houses a computer, a power supply, and other specialty electronics to control the wavefront generators 10. Images projected from the wavefront generators are reflected by field mirror 4 and viewed by the patient seated in the exam chair 8.

FIG. 4 shows a perspective view of the examination chair 2A of the IOL emulator that is located adjacent, and forward of, the vertical tower 1, and it is preferentially mechanically isolated from the tower 1 so that patient movements in the chair are not transmitted to the components in the tower. The examination chair has a seat portion 8, the position of which is adjustable through motor means located in the base of the chair 11 that may be made responsive to the system computer. The seat back has a head rest 12 that may be adjustable through manual or by automatic means made responsive to the system computer. Optional head restraint (not shown) may be deployed from the underside of optical tray 10 to aid in stabilizing the patient's head during the exam.

The examination chair has arm rests 13, each of which has a platform 14 for supporting patient input means 15. In one embodiment, the input means is a rotary haptic controller that the patient may rotate, translate, or depress to provide input to the system computer during the examination. Suitable haptic controllers are manufactured by Immersion Technologies, San Jose, Calif. 95131, and such controllers are particularly suited to providing intuitive input to the system during the exam. Numerous other input devices are known, such as a mouse, a joystick, a rotary control, touch-sensitive screen, voice, and other control means, any of which may be employed as alternative embodiments.

Figure 5:
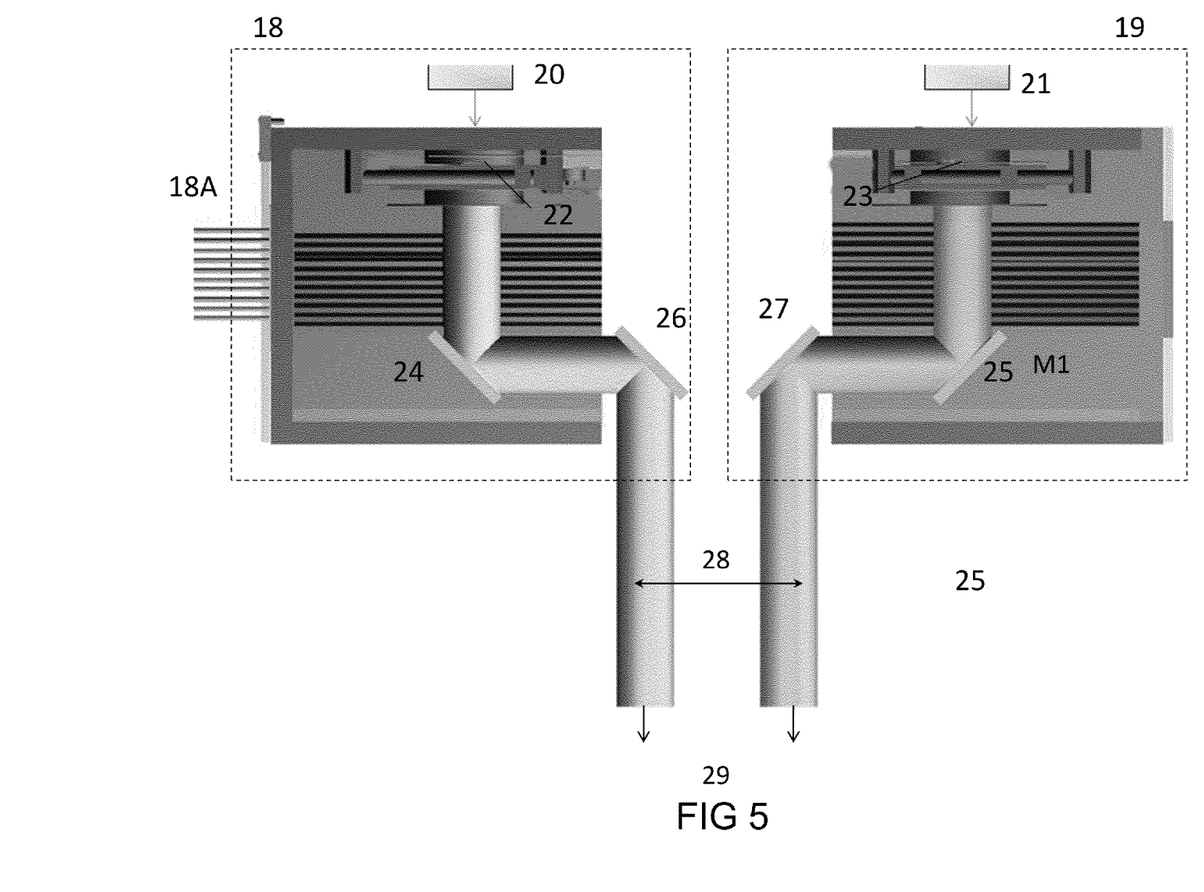
FIG. 5 is a partial top plan view of the wavefront generators for the right and left eyes with the adjustable optical elements removed.

FIG. 5 shows a top view of the wavefront generators for the right eye 18 and left eye 19 with the adjustable lenses and accessory lenses removed. Display means for the right eye 20 and left eye 21 generate images. One suitable image generating means is model SXGA OLED-XL™, made by EMagin Company, Bellevue, Wash. Numerous other image generating means and modalities are known in the art including LED, OLED, DLP, CRT and other means, any and all of which may be suitable for alternative embodiments.

Images generated by 20 and 21 pass through collimating lens 22 and 23. Collimated light of the images then traverses the stack of adjustable optical elements and accessory lens elements, shown in detail in FIG. 6, and described below, where they are redirected by beam turning mirrors 24 and 26 for the right eye, and by turning mirrors 25 and 27 for the left eye where they are then directed towards the field mirror 29. The position and angle of turning mirrors 24, 25, 26, and 27 can be made responsive to the system computer by actuator means (not shown) in order to direct the beam to the field mirror and to adjust the spacing between the left and right beam paths to that of the patient's inter-pupillary distance, 28. In a preferred embodiment, turning mirrors 24, 25, 26, and 27 may be made responsive to an eye and/or gaze tracking system to aid in directing the beam along the desired path for patient testing.

Suitable adjustable lenses for use in the wavefront generators are lenses described by Alvarez in U.S. Pat. No. 3,305, 294. In general, these lenses are comprised of two elements, each surface of which may be described by a cubic polynomial equation and each element is a mirror image of its fellow element. It is known to those skilled in the art that the coefficients of the equations that define the shape of the Alvarez lens elements may be optimized to improve their optical performance and to minimize undesirable aberrations, by, for example, using suitable optical design software such as ZeMax (Radiant ZEMAX LLC, 3001 112th Avenue NE, Suite 202, Bellevue, Wash. 98004-8017 USA). Such modifications of the adjustable lenses are fully envisioned within the scope of the present disclosure.

As the elements of the Alvarez lens pairs are made to translate relative to each other in a direction that is perpendicular to the optical axis of the element, the optical power imparted to an image passing through them changes as a function of the translation distance. The lenses are mounted in surrounding frames and they are translated by actuator means such as, by example, control cables 18A such that their motion is made responsive to the system computer. Alternate lens actuation means are known in the art and are within the scope of the present disclosure.

Other types of adjustable lenses and mirrors are known in the art that may be used in the wavefront generator to modulate the wavefront of an image and they are considered to be within the scope of the invention. Deformable mirrors that may be made responsive to a computer are known such as those manufactured by Edmunds Optics, 101 East Gloucester Pike, Barrington, N.J. 08007-1380. As an alternative embodiment, the adjustable Alvarez lenses described above may be replaced by fixed lenses, by one or more deformable mirrors, or by any combination of fixed lenses, deformable mirrors, and Alvarez lenses and remain under the scope of the present disclosure. Another embodiment involves the use of one or a plurality of discrete lenses, disposed in a rack or other arrangement, and used to modulate the wavefront of the image.

Figure 6:
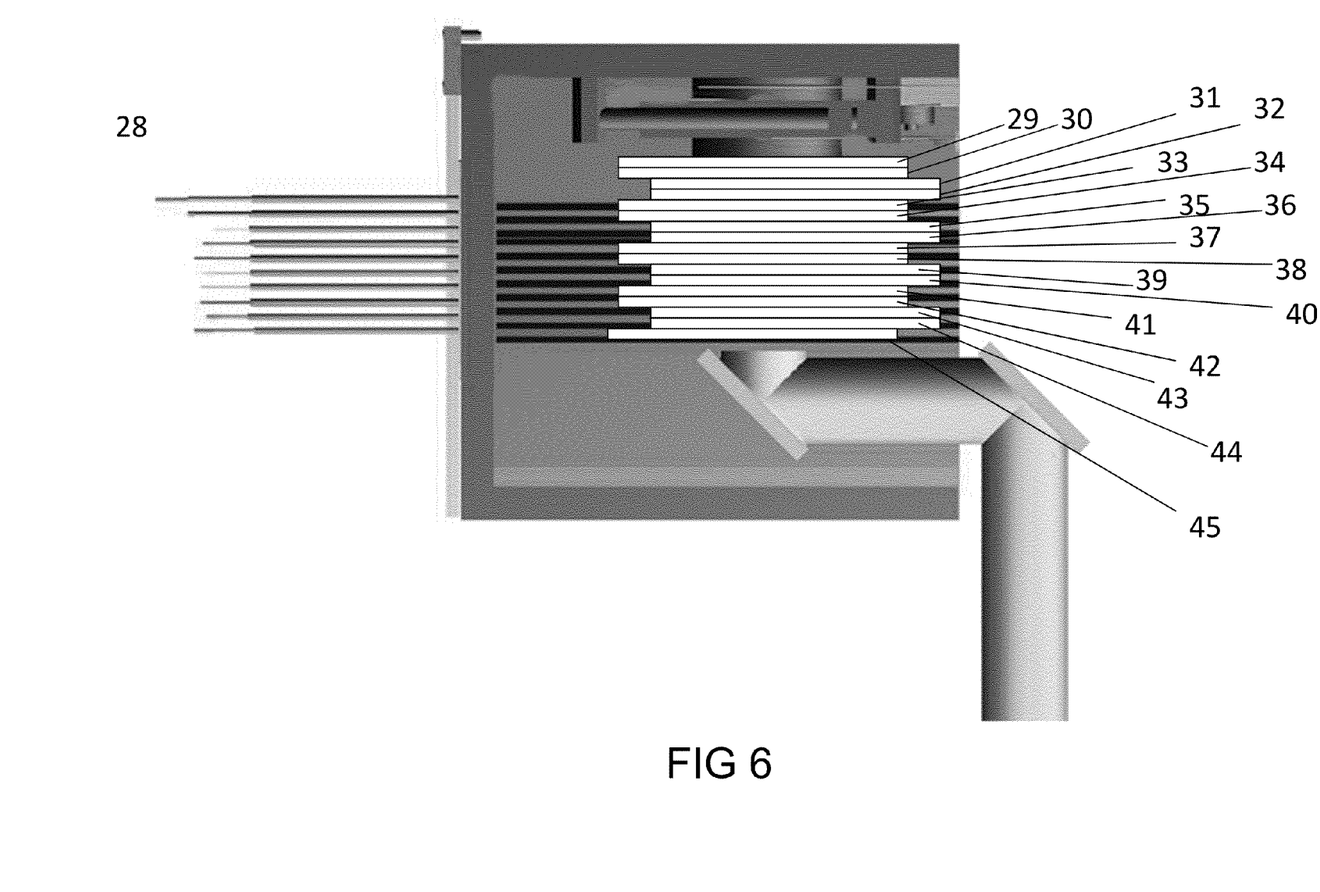
FIG. 6 is a partial detailed view of an embodiment of the wavefront generator for the right eye with the adjustable lenses in position

FIG. 6 shows a more detailed view of the wavefront generator for the right eye showing the adjustable Alvarez lens pairs and the accessory lens pairs 29-45 that are used to modify the wavefront of the image that is created by display means 20. The identity of these lenses of one embodiment is listed in FIG. 7.

Figure 7:
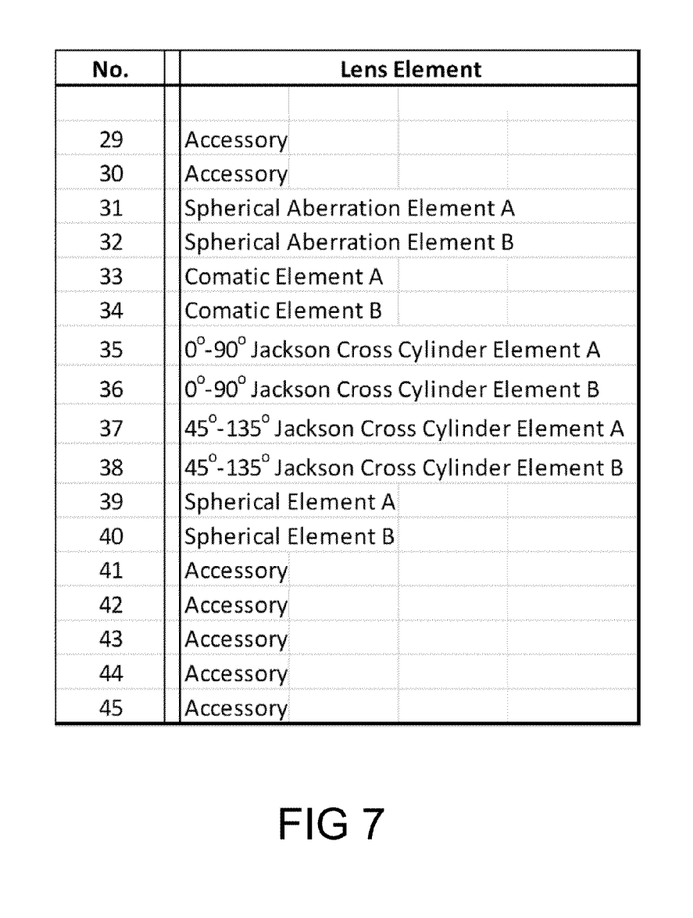
FIG. 7 is a table listing the identity of the adjustable lens elements shown in FIG. 6.

In general, it is envisioned that the optical elements listed in FIG. 7 will be selected to modulate the wavefront of an image in order to provide a full range of correction of refractive errors from −20D to +20D and astigmatic corrections up to, or beyond, 8D. In addition to providing spherical and cylindrical modulations to the wavefront, the lenses will be able to impart higher order aberrations to the wavefront including spherical aberration and comatic aberrations. As an alternative embodiment, the wavefront generator may utilize fixed and adjustable lens elements to impart spherical and cylindrical modulations to the wavefront, and employ deformable mirror elements to impart higher order aberrations to the wavefront of the image.

Phase plates, such as those prepared by lathing a PMMA or other suitable optical material into the desired shape, may be inserted in accessory slots 29, 30, and 41-45 of the wavefront generator in order to impart additional modulations to the wavefront that are not imparted by the adjustable optical components in order to effectively emulate the wavefront modulation of the IOL measured by the optical characterization system, D.

FIG. 3 shows a side view of the viewport 3, that houses the field mirror 4. In a preferred embodiment, the field mirror is round in shape and it has a spherical concave curvature with a radius of curvature approximately 2.5M and a diameter between 10" and 24." Such mirrors are known in telescopic applications and a suitable mirror may be procured from Star Instruments, Newnan, Ga. 30263-7424. Alternative embodiments for spherical mirrors are known such as CFRP (carbon fiber reinforced polymer) spherical rectangular mirrors which may be procured from Composite Mirrors Applications in Arizona. Alternative embodiments for the focusing system include the use of an aspheric mirror, a toroidal mirror, a mirror that is non-circular in shape, and a plano mirror.

In a preferred embodiment, the radius of curvature of the mirror 4 corresponds to the approximate distance between the spectacle plane of the patient's eyes (at the nominal testing position 9) to the mirror, and from the center of the wavefront generator 10 to the field mirror 4. It is known to those skilled in the art that an object located at a distance from a spherical concave mirror that is equal to the radius of curvature of the mirror, produces an image at a conjugate optical plane of the mirror with a magnification of one. Because the adjustable lenses and the spectacle plane are located at optical planes that are conjugate with respect to the field mirror, the adjustable lenses will have the same effective power at the patient's spectacle plane as they do in the wavefront generator. Stated differently, the field mirror optically relays the adjustable lenses in the wavefront generator to, or near, the patient's spectacle plane, while leaving the spectacle plane in front of the eye free of physical lenses or other instrumentation.

Operating the instrument at, or near, this condition of "unity magnification" is a preferred embodiment. However, it is known that changes in effective lens power that result from Alvarez lenses imaged from the wavefront generator to the spectacle plane at non-unity magnifications may be compensated for by calibration tables and/or by adjusting the adjustable optical elements in wavefront generator 10 to correct for the operation of the device at such non-unity magnifications. Such corrections may be made by the system computer automatically without the input by the operator. It is also known that only one location in the Alvarez stack can be at the center of curvature along the optical axis of the mirror, and that some correction factor(s) must be applied to the lenses in the wavefront generator that are located adjacent the center of curvature.

As shown in FIG. 3, a desk 5A is provided to support the display terminal 5 used by the operator to provide control inputs to the computer and to receive displays from the device. Operator input may be provided by conventional keyboard, mouse, or optional haptic means to control the IOL emulator during the examination. These devices are connected to the system computer through conventional cable, fiber optic, or wireless means.

Figure 8:
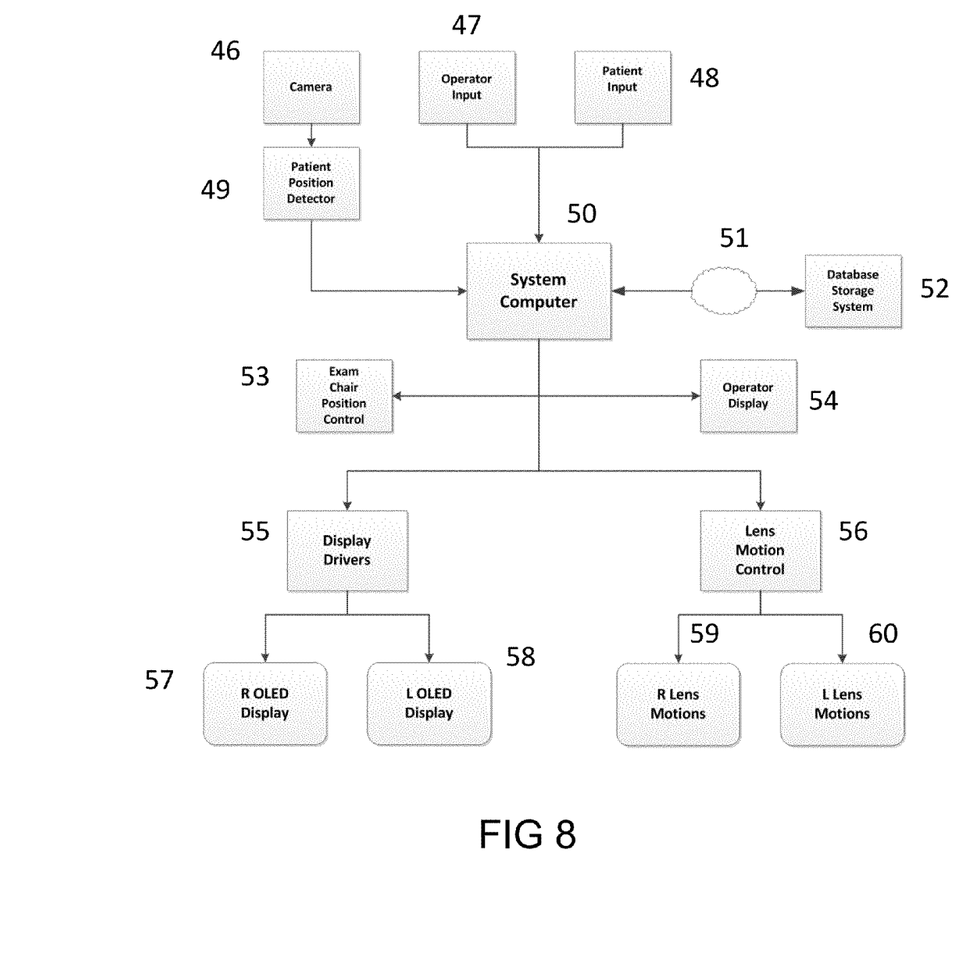
FIG. 8 is a block diagram of inputs and outputs of the System computer.

FIG. 8 shows inputs and outputs of the system computer 50 to different subsystems of the apparatus. Camera 46 provides information to the patient position detector 49, which provides input to system computer 50. Operator inputs 47 and patient inputs 48 are provided to the system computer.

The system computer 50 receives inputs and provides outputs to database storage system 52, which in a preferred embodiment may be transmitted through the Internet 51.

The system computer 50 provides outputs to display drivers 55 which run the digital displays 57 and 58, which in a preferred embodiment, may be organic light emitting diodes described above. The system computer 50 provides outputs to lens motion control system 56 which directs the actuators that drive the adjustable lenses for the right and left channels of the wavefront generators, 59 and 60, respectively. The lens motion control 60, also controls the positions of accessory lenses which may include phase plates that may be introduced into one or more of the accessory lens slots of the wavefront generator as shown in 29, 30 and 41-45, and described in more detail below.

Figure 9:
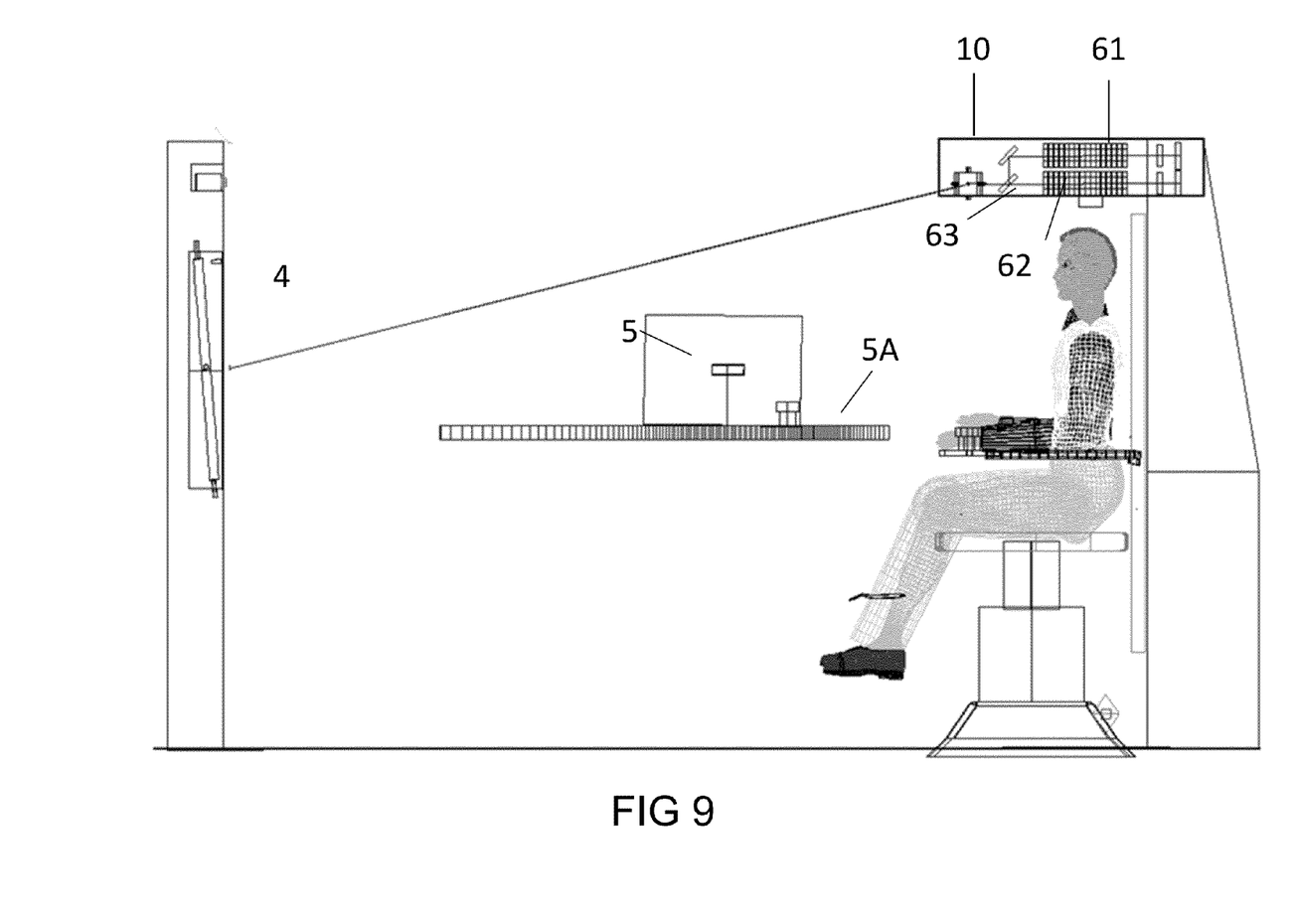
FIG. 9 is a diagrammatical side elevational view of a preferred embodiment of the invention in which the optical channels for each eye have two independent wavefront generators.

FIG. 9 shows a side view of a preferred embodiment in which two wavefront generators per eye, four total, are included in the apparatus. For the right eye channels, the images of upper wavefront generator 61 and lower wavefront generator 62 are combined by beam combining element 63 and thereafter directed out of the wavefront generator towards field mirror 4. As will be described below, a plurality of wavefront generators per eye allows for patients to view and compare the images produced by the emulated optical properties of IOLs of a different design on a side-by-side and simultaneous basis.

Figure 10:
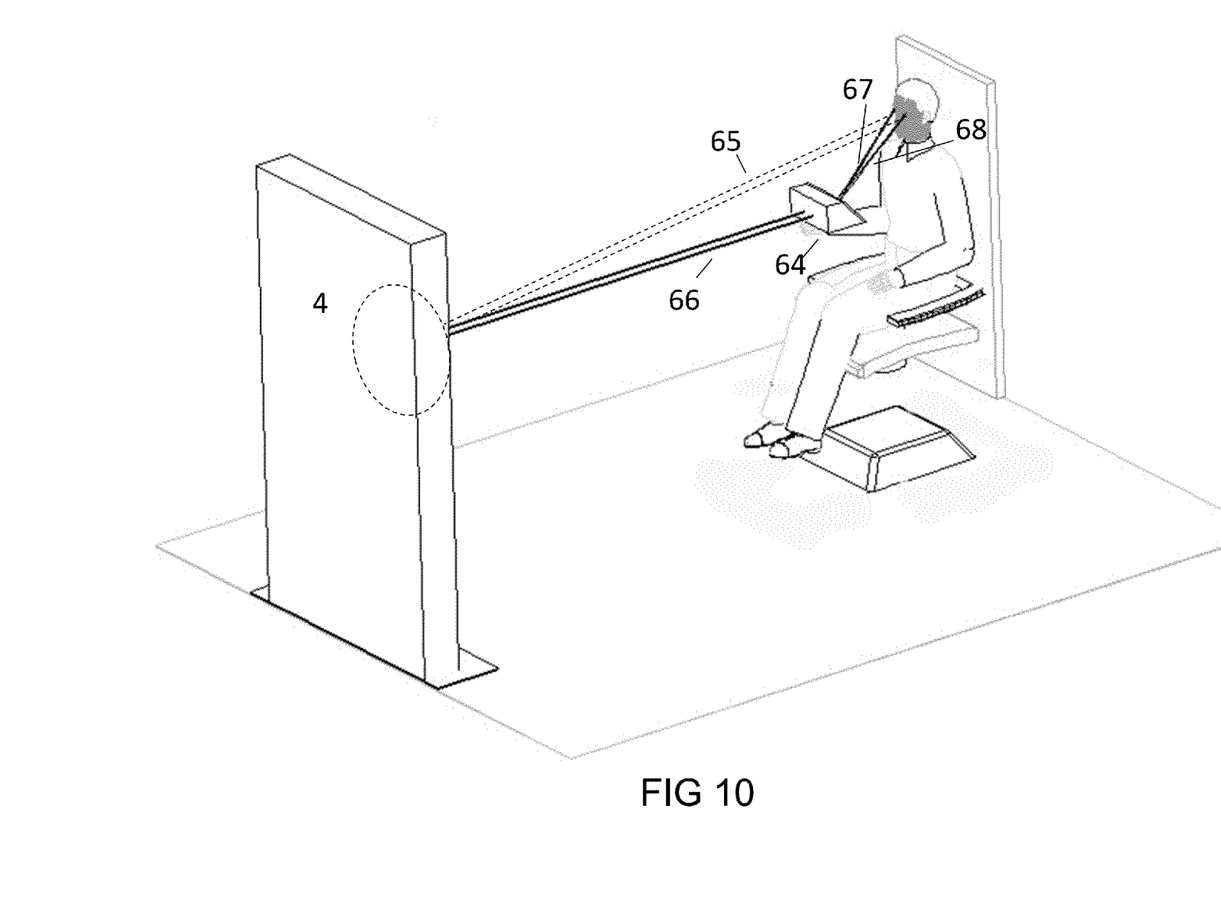
FIG. 10 is a diagrammatical front perspective view showing the near viewing accessory of the IOL emulator.

FIG. 10 shows a near-viewing display 64 of the focusing system of the apparatus. When the field mirror 4 is caused to redirect the path of the beam paths from 65 to 66, mirrors (not shown) inside the near viewing display 64 redirect the beams to the patient's eyes along paths 67 and 68. The mirrors cause the images to diverge with respect to one another, and to appear to the patient in the exam chair as if they emerged from the viewing surface 73 of the near viewing display 64.

Figure 11:
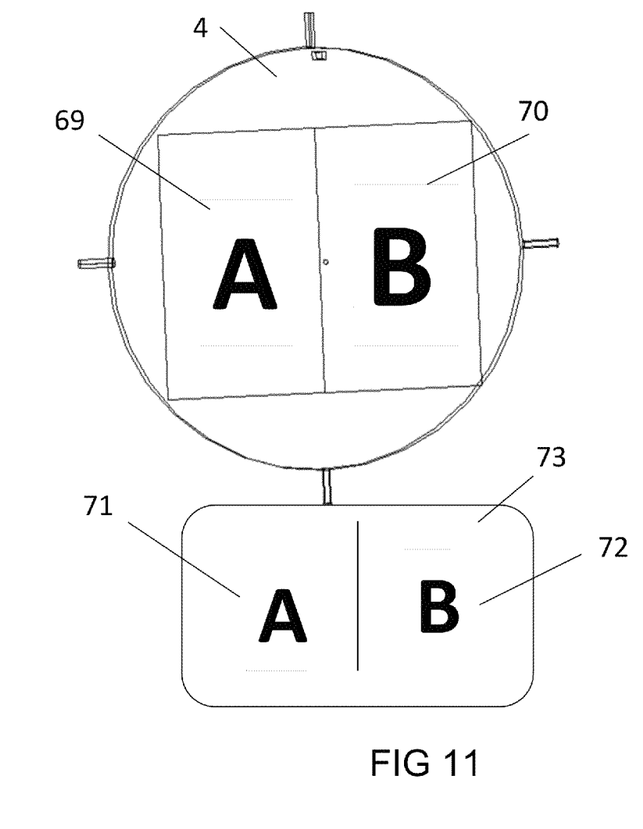
FIG. 11 depicts the patients monocular right eye view of the field mirror and near viewing accessory while the IOL emulator is generating images that emulate images formed by IOLs A and B, thereby allowing the patient to preview, compare, and select the IOL that provides the best vision.

FIG. 11 shows the patient's right eye view of the viewport 4 and the surface of the near viewing display 73. When an embodiment with two or more wavefront generators is employed, the patient is able to preview and compare images formed by emulation of wavefronts created by IOL A and IOL B on a side-by-side basis, at both near and distance viewing distances through the field mirror 4 and the surface 73 of the near viewing display 64.

The use of the apparatus to determine the optical characteristics of a plurality of IOLs and the emulation of the performance of those IOLs in a prospective implant patient will now be described.

It is known to those skilled in the art that when opacities develop in the crystalline lens, the optical properties of the eye change, including the eye's refractive and transmissive characteristics. Because this disclosure envisions testing the eye before the crystalline lens has been removed during a cataract procedure, those skilled in the art will recognize that it is preferred to use the disclosed method and apparatus before the patient's cataract has advanced to the point that the patient is unable to perceive the differences in image quality that different IOLs designs provide.

Three IOLs of three different designs are shown as A, B, and C in FIG. 1. The optical properties of each IOL are measured by IOL measuring means D, and these wavefronts are represented by mathematical functions $E_a$, $E_b$, and $E_c$, respectively. These mathematical functions describe the three dimensional shape of a wavefront of light at a particular distance after it passes through the IOL. Suitable functions for describing this wavefront include a Zernicke polynomial expansion series, a Fournier function, or similar mathematical expressions. Optionally, optical properties in addition to the phase change that are imparted by the IOLs can be measured, for example, the transmission of light as a function of wavelength and this information can be used to increase the fidelity of the emulation of the IOL by the wavefront generator.

It is known to those skilled in the art that the crystalline lens of the eye imparts primarily a positive spherical optical power. Because the emulation of the IOL's properties with the apparatus is to be conducted in an eye that usually has a crystalline lens with its attendant spherical power intact, it is necessary to subtract the spherical component of the wavefront from the total measured optical power of the IOLs that have been measured and that are represented by functions $E_a$, $E_b$, and $E_c$.

In FIG. 1 the subtraction of the spherical optical power from the total power measurement of the IOLs is shown as operation F, and this operation yields new mathematical functions $E'_a$, $E'_b$, and $E'_c$. These functions represent the residual optical power of the IOLs after their spherical power has been subtracted. This value is referred to herein as the IOL residual aspheric optical power. Optionally, optical properties in addition to the phase change that are imparted by the IOLs can be added to the wavelength generator to increase the fidelity of the emulation of the IOL by the wavefront generator. For example, an appropriate neutral density filter can be added to the wavefront generator to replicate the spectral transmission properties of a particular IOL to be emulated.

Next, it is necessary to determine if the aspheric powers $E'_a$, $E'_b$, and $E'_c$ of the IOLs can be emulated by the adjustable optical components of the wavefront generator that are listed in FIG. 7. In general, for IOLs of refractive designs that have contiguous power transitions, it may be possible to emulate the IOL power with a combination of adjustable Alvarez lenses and deformable mirrors. However, for diffractive IOLs that employ Fresnel optics and for refractive designs that have abrupt changes in optical power between zones, it may be necessary to procure a phase plate of PMMA or other suitable optical material that, when placed in series with the adjustable optical elements in the wavefront generator will result in an accurate emulation of the optical properties of the IOL.

In general, the shape of the phase plate required can be determined by subtracting the closest-fit wavefront that can be generated by the adjustable lenses listed in FIG. 7 from the residual aspheric power of the IOL measurement, for example, $E'_a$, $E'_b$, and $E'_c$, described above.

Once the necessary phase plate(s) has been procured, if required for the for the IOL(s) to be emulated, the emulation of the IOL in a prospective implant patient may proceed as described above.

In an alternative embodiment, the actual IOL to be emulated is placed into the wavefront generator by placing it in an appropriate containment holder and interposing it in the wavefront generator in the appropriate location, such as accessory slot 29 shown in FIG. 6. Various embodiments of the apparatus allow placing the IOL in air or in a suitable fluid.

The adjustable optical elements in the wavefront generator 18 are first adjusted to neutralize the refractive errors of the patient's visual system in the eye being testing. Next, the adjustable optical elements in the wavefront generator are interposed in the beam path to emulate the optical properties of the IOL as if the IOL were implanted in the lenticular plane of the eye following removal of the eye's crystalline lens.

When an image produced by image generation means 20 traverses the wavefront generator 18, and is focused by the field mirror 4, it will appear to the patient as if the image passed through the IOL after the IOL replaced the patient's crystalline lens. Stated differently, to a patient viewing a distant object in mirror 4, the object would appear as if light rays from the object passed through the IOL after it was implanted in the patients eye, following removal of the eye's crystalline lens.

Assessing the quality of vision for both near, distant, and intermediate viewing distances is desirable for patients to evaluate the performance of presbyopia-correcting IOLs FIG. 10 shows the patient viewing near images in the apparatus. For near-image viewing, field mirror 4 is tilted down in order to re-direct the light beams from paths 65 to paths 66, which causes them to pass through near-viewing assembly 64.

For near viewing, the adjustable spherical lenses in the wavefront generators 18 and 19 are adjusted to impart the appropriate divergence to the wavefront of the image that is associated with the near viewing distance. For example, to properly emulate the viewing of an image that emerges from the viewing surface 73 of near viewing assembly 64 when it is located 25 cm from the patient's eyes, approximately −4D of spherical lens power would be added to the pre-existing settings of the adjustable optical elements in the wavefront generator and this −4D of divergence is then optically relayed to the patient's spectacle plane by the field mirror as described above. To the patient, it will appear as if the image is emerging from the surface 73 of the near viewing assembly.

In a preferred embodiment, the field mirror 4 is made responsive to an eye and gaze tracking system which receives inputs from camera(s) 4A. When the eye and gaze tracking system detects that the patient's gaze is directed downward to the viewing surface 73 of the near viewing assembly 64, the field mirror 4 is tilted downward so that it redirects the beams from paths 65 to 66, thereby causing them to pass through the near viewing assembly 64.

FIG. 11 shows the patient's right eye view of the field mirror 4 and the near viewing surface 73 of the near viewing assembly 64. The wavefront generator 61 is producing image A through the necessary combinations of optical elements required to emulate the optical properties of IOL A, and wavefront generator 62 is producing image B through the necessary combinations of optical elements required to emulate the optical properties of IOL B.

Thus, the patient can preview, compare, and select the IOL optics of either IOL A or IOL B that provides the best quality of image. These images may be compared simultaneously on a side-by-side basis. Similarly, when viewing the near viewing surface 73, images A and B are produced in a similar fashion by redirecting field mirror 4 and by adjusting the adjustable lenses in the wavefront generator to generate the appropriate divergence of light for the viewing distance of viewing surface 73 of the near viewing assembly 64.

By activating the wavefront generators for the left eye, a binocular comparison of images A and B can be attained.

The disclosure above provides many useful inventive features over prior art methods.

Means are provided to characterize the optical properties of any IOL, and to accurately emulate those optical properties in a prospective implant patient under realistic viewing conditions over near, intermediate, and far away distances. This allows the prospective implant patient to preview, compare, and select a particular IOL design that they prefer based upon the patient's subjective appraisal.

Unlike prior art methods, the present apparatus and method provide the ability to compare the performance of different IOL designs over a variety of viewing distances under natural viewing conditions free of obstructing optical instrumentation. Since a major benefit of a presbyopia-correcting IOL design is to provide clear vision over the typical range of viewing distances, the device provides a useful means for the patient to test the performance of the IOL design over the full range of viewing distances that the patient requires.

Another novel feature of the present apparatus and method is its ability for patients to assess the performance of various IOL designs over a range of image illuminations, colors, and contrasts. By adjusting the output of the image projectors, patients can see how the different IOL designs compare as illumination and contrast rises or falls and as colors change. No prior art method offers this ability.

The novel capabilities provided by this device will allow doctors to determine which patients are good candidates for a presbyopia correcting IOL, or other type of IOL, and which are not, and it will provide information that is useful to select the particular type of IOL that is most likely to provide the patient with the most satisfactory visual outcome.

The emulation of IOLs of diffractive and refractive designs was described above. The actual accommodative amplitude of accommodating lenses can also be measured and emulated in the apparatus by adjusting the spherical power lenses in the wavefront generator when the patient views a near object. Thus, the device has utility in its novel capability to characterize and emulate IOLs of existing and future designs, including IOLs that change in shape or position during the viewing of near objects.

Another novel feature is the ability to stabilize the image into the appropriate image plane by using an eye and gaze tracker. This relieves the patient of the need to hold still during the test and it facilitates a more realistic emulation of IOL performance under natural viewing conditions.

We claim:

1. A method of vision testing that allows a patient to preview the optical properties of an intra-ocular lens implant to correct the patient's vision following removal of the patient's crystalline lens, comprising the steps of: a. determining the optical properties of an IOL to be emulated; b. generating a static or dynamic (movie) image viewable by a patient; c. modulating the wavefront of the image to produce an image on the patient's retina that emulates the image that would result following removal of the patient's crystalline lens and implantation of the intra-ocular lens to be emulated.

2. The method of claim 1 in which modulating the wavefront of the image is performed remotely from the patient.

3. The method of claim 1 in which a plurality of IOLs are emulated simultaneously.

4. The method of claim 1 in which said modulating step includes interposing an intra-ocular lens in said wavefront generator and projecting said image through said intra-ocular lens.

5. The method of claim 1 in which said modifying step is responsive to inputs provided by the patient.

6. A vision testing apparatus that allows a patient to preview, compare, and select an intra-ocular lens implant that corrects the patient's vision following removal of the patient's crystalline lens, comprising:
   means for projecting an image from a wavefront generator through optical elements that are under control of a computer;
   means for focusing said image to a position optically conjugate to the patient's eye;
   means for nulling the refractive error of the visual system of the eye being tested; and
   means for adjusting the wavefront generator to produce an image on the patient's retina that emulates the image that would result from implantation of the intra-ocular lens.

7. The apparatus of claim 6 including means for modifying the image produced by the wavefront generator for correcting refractive errors.

8. The apparatus of claim 7 in which said means for modifying the image is responsive to input provided by the patient.

9. The apparatus of claim 7 including one or more intra-ocular lenses that are interposed in said wavefront generator for projecting said image through said one or more intra-ocular lenses.

10. The apparatus of claim 6 including one or more intra-ocular lenses interposed in said wavefront generator for projecting said image through said intra-ocular lenses.

11. The method of claim 6 including input means for adjusting of the wavefront generator image in response to input from the patient.

* * * * *